United States Patent
Slick (10) Patent No.: US 9,738,297 B2
(45) Date of Patent: Aug. 22, 2017

(54) MULTIPLE USE ASSISTIVE CART

(71) Applicant: Brooke Slick, New Enterprise, PA (US)

(72) Inventor: Brooke Slick, New Enterprise, PA (US)

( * ) Notice: Subject to any disclaimer, the term of this patent is extended or adjusted under 35 U.S.C. 154(b) by 0 days.

(21) Appl. No.: 15/205,812

(22) Filed: Jul. 8, 2016

(65) Prior Publication Data

US 2017/0015341 A1    Jan. 19, 2017

Related U.S. Application Data

(60) Provisional application No. 62/192,898, filed on Jul. 15, 2015.

(51) Int. Cl.
| | |
|---|---|
| *B62B 3/10* | (2006.01) |
| *B62B 3/02* | (2006.01) |
| *B62B 5/06* | (2006.01) |
| *A61B 50/13* | (2016.01) |
| *A61G 12/00* | (2006.01) |

(52) U.S. Cl.
CPC .............. *B62B 3/025* (2013.01); *A61B 50/13* (2016.02); *A61G 12/001* (2013.01); *B62B 3/10* (2013.01); *B62B 5/06* (2013.01)

(58) Field of Classification Search
CPC .. B62B 1/04–1/047; B62B 3/02–3/027; B62B 3/08–3/108; A61B 50/13–50/15; A61G 12/00–12/002; A61G 12/008
See application file for complete search history.

(56) References Cited

U.S. PATENT DOCUMENTS

| | | | | |
|---|---|---|---|---|
| 2,212,053 A | * | 8/1940 | Smith ................... | B62B 3/027 280/3 |
| 2,419,422 A | * | 4/1947 | Schulein ................. | B62B 3/10 211/182 |
| 2,555,178 A | * | 5/1951 | Young .................... | A47L 13/50 211/1 |
| 3,722,905 A | * | 3/1973 | Solomon ................. | B62B 3/02 211/200 |
| 3,856,320 A | * | 12/1974 | Blanchard ................ | B62B 3/02 211/187 |
| 3,923,167 A | * | 12/1975 | Blankenbeckler ....... | B25H 1/00 414/11 |
| 4,065,179 A | * | 12/1977 | Takasaki ................ | A47K 11/04 297/464 |
| 4,266,765 A | * | 5/1981 | Sandoval ............... | A61G 12/00 280/47.371 |
| 4,493,492 A | * | 1/1985 | Balabanova ............. | B62B 3/10 15/260 |
| 4,505,495 A | * | 3/1985 | Foss ........................ | B62B 3/02 16/113.1 |
| 4,531,752 A | * | 7/1985 | Diener .................... | B62B 1/10 211/189 |
| 4,586,721 A | * | 5/1986 | Harada .................... | B62B 7/12 280/30 |
| 4,790,549 A | * | 12/1988 | Armand ................... | B62B 1/12 211/186 |

(Continued)

*Primary Examiner* — Erez Gurari (57) ABSTRACT

Described herein is a multiple use assistive cart to aid in a users mobility. The cart includes a base portion with a plurality of wheels for movement and a center portion with a plurality of apertures. The apertures allowing for the attachment of multiple assistive devices including but not limited to, baskets, bags, IV holders, oxygen holders, and other similar items.

13 Claims, 7 Drawing Sheets

(56) References Cited

U.S. PATENT DOCUMENTS

| | | | | |
|---|---|---|---|---|
| 4,795,186 A * | 1/1989 | Tyus | ............... | B62B 3/02 280/37 |
| 4,896,897 A * | 1/1990 | Wilhelm | ............... | B62B 1/002 280/47.2 |
| D328,316 S * | 7/1992 | Rogers | ............... | 280/87.041 |
| 5,326,116 A * | 7/1994 | Flax | ............... | B62B 3/02 280/47.29 |
| 5,505,471 A * | 4/1996 | Cheng | ............... | B62B 1/047 280/30 |
| 5,641,170 A * | 6/1997 | Helm | ............... | A47F 5/108 280/30 |
| 5,779,252 A * | 7/1998 | Bolton, Jr. | ............... | B62B 3/02 280/35 |
| 5,816,604 A * | 10/1998 | Hsieh | ............... | B62B 3/02 280/33.997 |
| 5,863,055 A * | 1/1999 | Kasravi | ............... | B62B 5/0023 280/47.19 |
| 5,876,049 A * | 3/1999 | Spear | ............... | B62B 3/02 280/33.998 |
| 5,927,514 A * | 7/1999 | Linder | ............... | G12B 9/08 211/189 |
| 6,000,712 A * | 12/1999 | Wu | ............... | B62B 3/022 280/47.34 |
| 6,264,220 B1 * | 7/2001 | Pierce | ............... | B25H 3/04 280/47.35 |
| 6,783,147 B1 * | 8/2004 | Green, Sr. | ............... | B62B 1/20 280/47.26 |
| 7,004,482 B1 * | 2/2006 | Steffan | ............... | A63B 55/00 280/47.17 |
| 8,641,056 B1 * | 2/2014 | Carter | ............... | A45F 3/10 280/30 |
| D700,706 S * | 3/2014 | Molter | ............... | D24/185 |
| 8,814,181 B1 * | 8/2014 | Weldon | ............... | B62B 3/02 280/30 |
| 8,840,175 B2 * | 9/2014 | Short | ............... | A47B 85/04 297/119 |
| 8,936,257 B2 * | 1/2015 | Kinnee | ............... | A45C 5/146 16/44 |
| 8,944,444 B1 * | 2/2015 | Tvrdy | ............... | B62B 3/005 280/47.35 |
| 9,073,471 B1 * | 7/2015 | McIntosh | ............... | B60P 3/07 |
| 9,079,598 B1 * | 7/2015 | Oreyang | ............... | B62B 3/022 |
| 9,150,234 B2 * | 10/2015 | Beaver | ............... | B62B 3/10 |
| 9,499,186 B1 * | 11/2016 | Fink | ............... | B62B 3/02 |
| 9,586,604 B2 * | 3/2017 | Vanderberg | ............... | B62B 1/047 |
| 2003/0062700 A1 * | 4/2003 | Stallbaumer | ............... | B62B 1/002 280/47.27 |
| 2004/0090028 A1 * | 5/2004 | Trogstam | ............... | A01K 1/031 280/79.3 |
| 2005/0242549 A1 * | 11/2005 | Longenecker | ............... | B60N 2/2842 280/642 |
| 2006/0091628 A1 * | 5/2006 | Cheslak | ............... | A63C 11/026 280/47.27 |
| 2006/0182578 A1 * | 8/2006 | Morton | ............... | B62B 3/04 414/537 |
| 2009/0189498 A1 * | 7/2009 | Catron | ............... | B62B 3/02 312/249.8 |
| 2009/0224495 A1 * | 9/2009 | Anderson | ............... | B62B 3/027 280/47.26 |
| 2010/0066057 A1 * | 3/2010 | Jian | ............... | B62B 3/02 280/639 |
| 2011/0052357 A1 * | 3/2011 | Torrison | ............... | B62B 3/008 414/495 |
| 2012/0091675 A1 * | 4/2012 | Al-Hasan | ............... | B62B 3/04 280/47.371 |
| 2012/0193894 A1 * | 8/2012 | Fine | ............... | B62B 3/027 280/651 |
| 2012/0261907 A1 * | 10/2012 | White | ............... | B62B 5/067 280/651 |
| 2013/0056962 A1 * | 3/2013 | Liu | ............... | B62B 5/067 280/651 |
| 2014/0183832 A1 * | 7/2014 | Wang | ............... | B62B 3/022 280/39 |
| 2014/0183844 A1 * | 7/2014 | Iryami | ............... | B62B 3/027 280/659 |
| 2015/0176273 A1 * | 6/2015 | Farouk | ............... | E04B 2/7422 280/639 |
| 2016/0236700 A1 * | 8/2016 | Riha | ............... | B62B 1/002 |
| 2017/0015341 A1 * | 1/2017 | Slick | ............... | B62B 3/025 |

* cited by examiner

MULTIPLE USE ASSISTIVE CART

CROSS REFERENCE TO RELATED APPLICATIONS

This application claims priority to U.S. Provisional Patent Application No. 62/192,898 filed 15 Jul. 2015 to the above named inventor, and is herein incorporated by reference in its entirety.

FIELD OF THE INVENTION

The invention relates generally to a multiple use assistive cart.

BACKGROUND

Often individuals are required to carry multiple objects while walking. Typically, these users will utilize bags or carts to provide assistance to carrying these multiple objects. This need for assistance is particularly necessary for individuals who need help and support during walking or whom are suffering from a medical condition requiring them to transport medical supplies, such as IV's and oxygen, concurrently. Many of the currently available solutions do not meet the needs of the market as they only provide for a single use, such as support or transport. Therefore, there is a need in the market for a multiple use assistive cart. The cart is easily transported and configured to offer both support and space for the storage of various articles. Preferably, this cart is adaptable for these multiple uses and constructed out of durable and robust materials.

SUMMARY OF THE INVENTION

It would be advantageous to have an apparatus that can be used to carry medical equipment like an Oxygen tank or IV bag but also be adaptable for everyday uses. Furthermore, it would also be advantageous to have an apparatus that had 360-degree spinning wheels. Preferably these wheels include a resilient member that allows for shock absorption and wherein the wheels are capable of maneuvering on rough and uneven surfaces. Therefore, there currently exists a need in the market for an apparatus that provides a multiple use assistive cart to further aid in the mobility of a user.

The invention advantageously fills the aforementioned deficiencies by providing multiple use assistive cart, which provides the ability to carry items, aid and support an individual in walking, and transport medical equipment.

The multiple use cart of the present invention provides 360 degrees of fluid maneuverability. The cart includes a wide telescoping handle with an incorporated hand brake for slowing or locking the cart into a stationary position. The handle is movable in a vertical direction relative to a surface the cart is placed upon and received within a center portion of the cart. The center portion is comprised of durable polycarbonate and includes a plurality of keyhole-shaped openings that will accommodate a number of useful and removable attachments for the user. Additionally, the center portion includes a holder near the handle end that also serves as securing means for a cane or assistive walking device and additionally provides a means to confine and organize oxygen tank tubing and accessories. An I.D. tag compartment is securely concealed at the top of the center portion. The center portion may additionally include a hinged ring that is movable from a stored to a used position, wherein the ring is primarily sized and shaped to receive an oxygen bottom.

A side of the center portion opposite the openings may include a drop-down and latched panel primarily designed for the storage of a lid sized and shaped to the basket.

A base of the cart is hingedly affixed to a lower portion of the center portion of the cart, wherein the base can be folded up and locked into place for easy storage in the trunk of a car, in the closet of an airplane (just as they do for walkers), or any slim storage place. Side handles on the center portion make it easy for the user to handle the cart when placing it into and out of a storage spot. This base may include a molded ring sized to replace the hinged ring affixed to the center portion.

The apparatus has optional attachments that can be affixed to the cart within the keyhole-shaped slots of the center portion. The attachments include, but are not limited to, a basket and lid for everyday use, an office basket for the accommodation of paperwork, folders, electronics, small and large mesh-type bags for the transport of items for shopping, laundry, etc., an IV pole holder, and an oxygen tank holder. In the preferred embodiment of the present invention, the baskets and bags are shaped to fit the cane holder opening that would allow oxygen users to thread their tubing through and up to their face. Preferably, the baskets are made of metal mesh and the bags are made of heavy-duty cloth mesh.

The apparatus has fluid maneuverability.

The apparatus fulfills the need for an easy to use multi use assistive cart.

Among other things, it is an advantage of the invention to provide a multi-use assistive cart that does not suffer from any of the problems or deficiencies associated with prior solutions.

It is still further an advantage of the invention to provide security and convenience.

The invention now will be described more fully hereinafter with reference to the accompanying drawings, which are intended to be read in conjunction with both this summary, the detailed description and any preferred and/or particular embodiments specifically discussed or otherwise disclosed. This invention may, however, be embodied in many different forms and should not be construed as limited to the embodiments set forth herein; rather, these embodiments are provided by way of illustration only and so that this disclosure will be thorough, complete and will fully convey the full scope of the invention to those skilled in the art.

DETAILED DESCRIPTION OF THE INVENTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus.

These terms are not meant to limit the elements that they describe, as the various elements may be oriented differently in various applications.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

The invention is directed to be a multi-use assistive cart.

The invention is a mobility device with multiple configurations.

Referring to the figures, FIG. 1-7 show the multiple-use assistive cart to aid in mobility according to the present invention and generally referred to as cart 10. The cart 10 generally is provided with a center portion 100 and a base portion 200. The base portion 200 hingedly coupled to the center portion 100 through a hinge 202 and movable to a folded position parallel to the center portion 100 during storage and an extended position perpendicular to the base portion 100 during use. In this extended position, the base portion 200 is positioned parallel to a surface the cart 10 is placed upon with the center portion 100 extending a height opposite the base portion 200 and perpendicular to the surface. In this extended position, the center portion 100 provides for resting support during use by a user and allows the user to utilize the device 10 as a walking aid and for carrying assistance.

Figure 1:
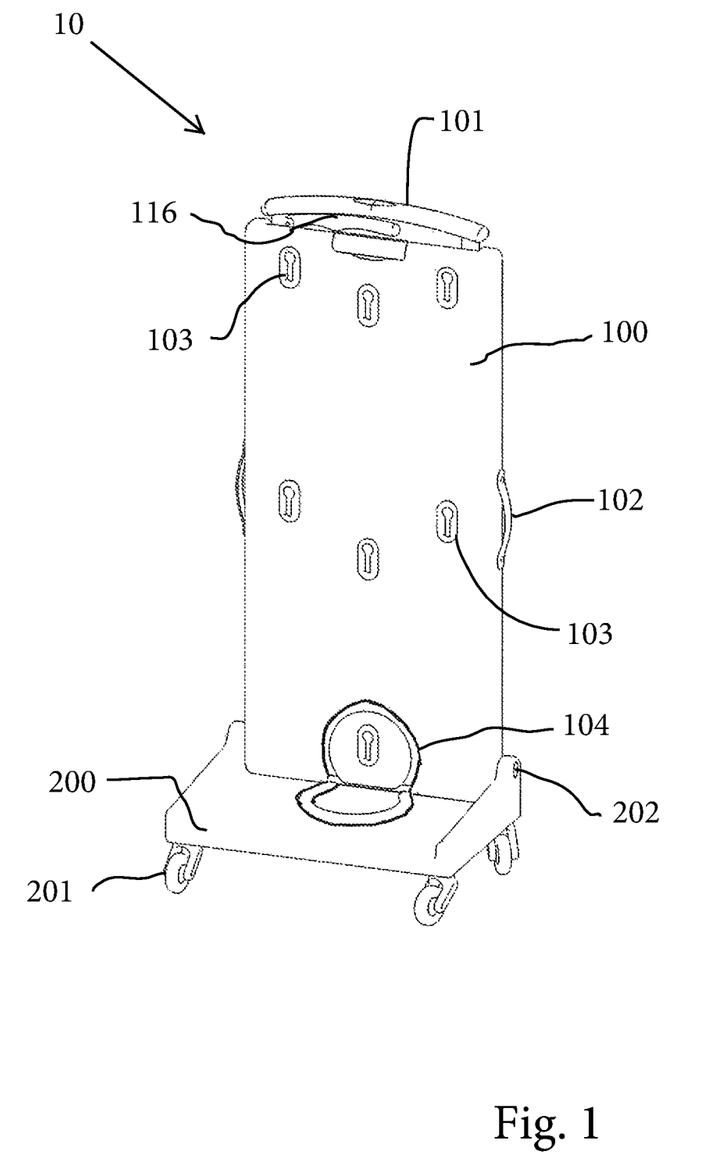
FIG. 1 shows an isometric view of the multi-use assistive cart, according to the present invention.
Figure 2:
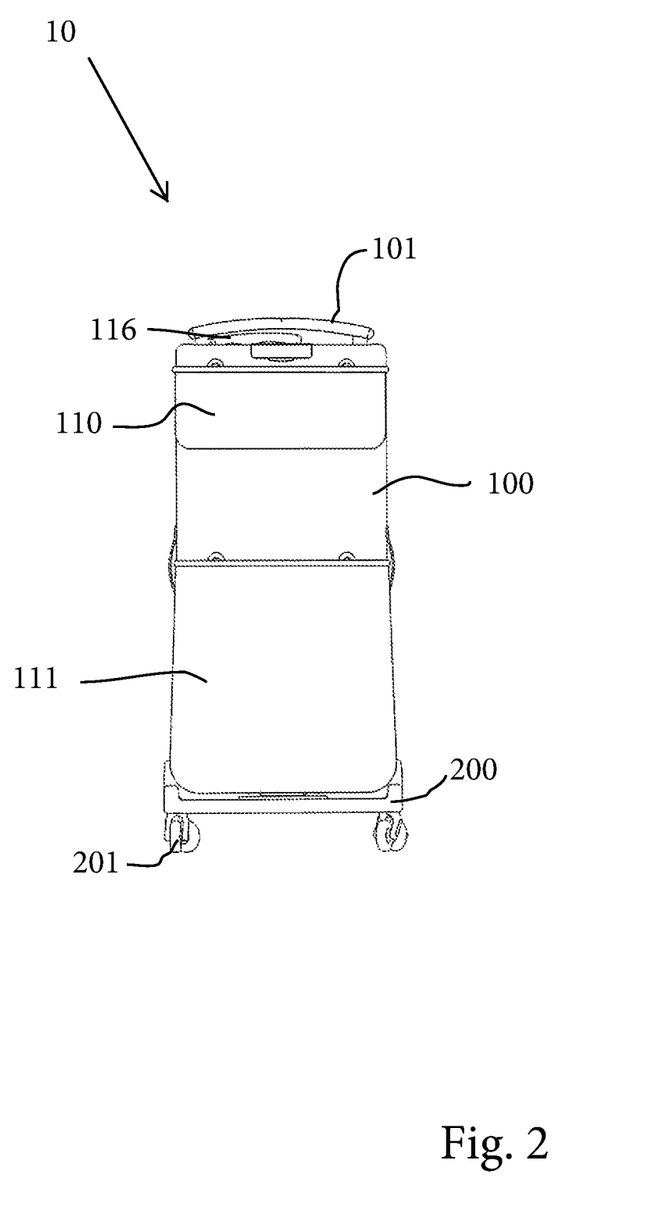
FIG. 2 shows a front side view of the cart with basket attachments, according to the present invention.
Figure 3:
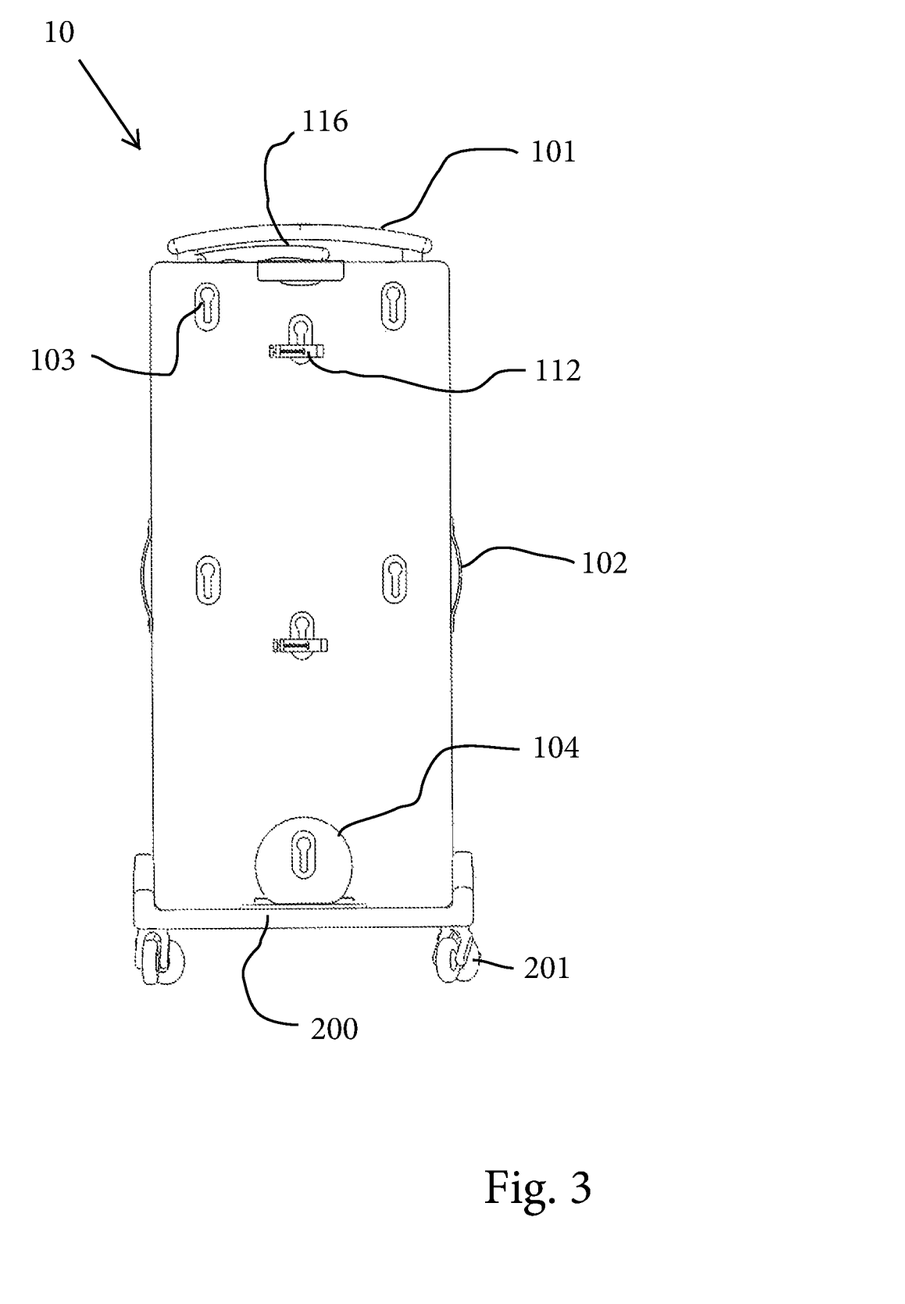
FIG. 3 shows a front side view of the cart with IV attachments, according to the present invention.
Figure 4:
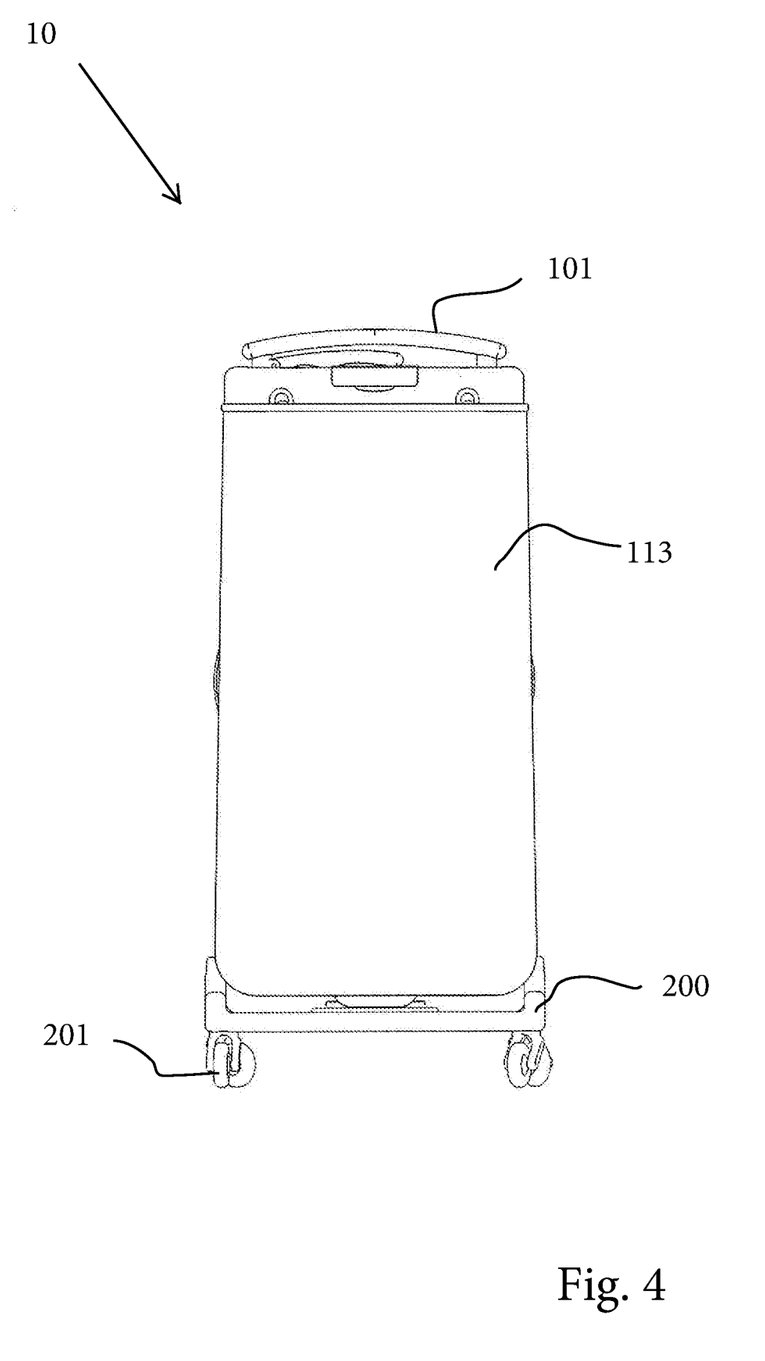
FIG. 4 shows a front side view of the cart with large bag attachment, according to the present invention.
Figure 5:
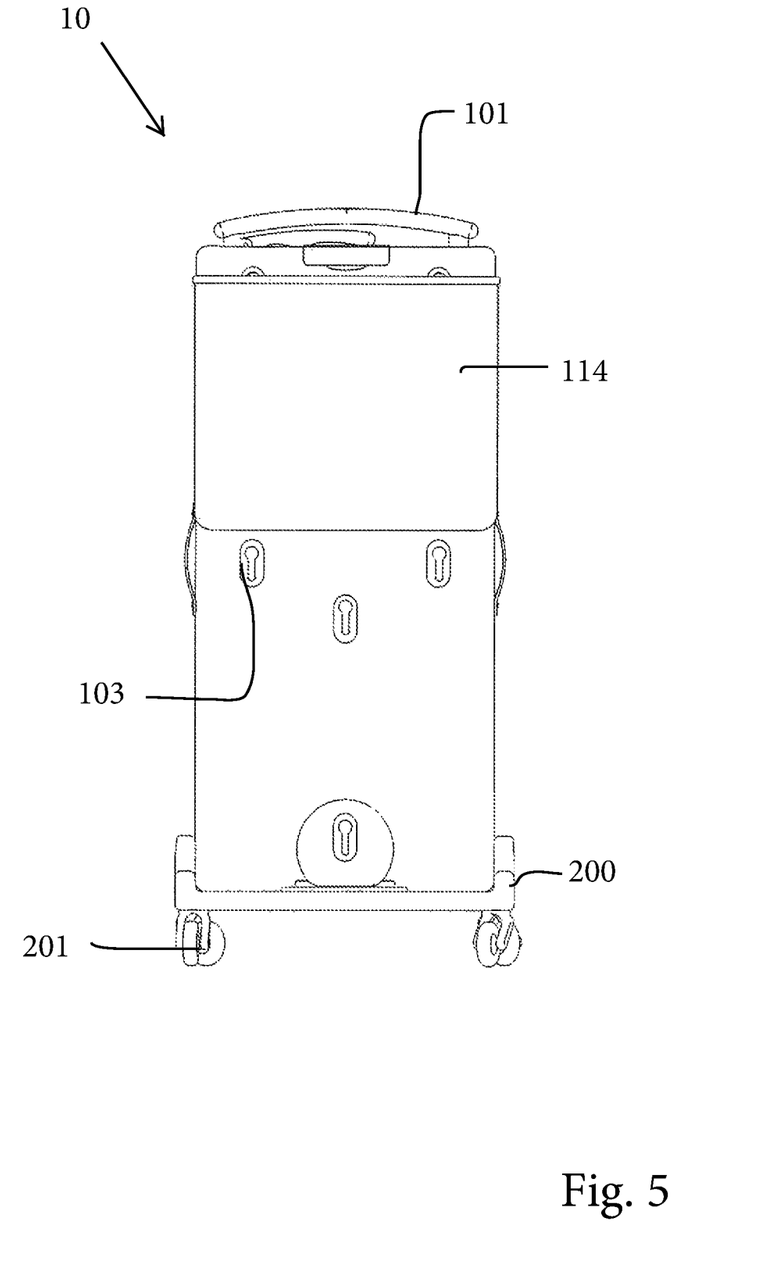
FIG. 5 shows a front side view of the cart with small bag attachment, according to the present invention.

The center portion 100 includes a top side, the top side opposite the coupling to the base portion 200 and including a handle 101, the handle 101 allowing for grasping support of a users hand during use. The handle 101 is nestedly received within an interior of the center portion 100 and movable to a desired height, wherein the handle 101 is adjustable in a vertical direction relative to the center portion 100 in the extended position to accommodate varying sizes/heights of a user. The handle 101 underside includes a brake 116. The brake 116 in communication with the surface and capable of arresting movement of the cart 10 through the application of a grasping force and temporarily securing the cart 10 in a fixed location.

A plurality of wheels 201 are positioned on an underside of the base portion 200 opposite the center portion 100 and designed for contacting the surface the cart 10 is placed upon. The wheels 201 are preferably of a caster type to allow for ease of mobility of the cart and include locking features and are provided in four separate locations along the underside of the base portion 200. Accordingly, and preferably, wheels 201 are located at each corner of the base portion 200, wherein the wheels 201 are spaced apart to allow for adequate balance, support, and mobility of the cart 10. The wheels 201 may be provided of a suitable and durable material and may additionally include a resilient member. The resilient member allowing the wheels 201 flexibility in motion and providing for shock absorptive properties.

The center portion 100 further including a side handle 102 to aid in usage and in carrying when the device 10 is in the folded position. The side handle 102 provides a grasping surface allowing a user to easily manipulate the device 10 in this folded position.

Figure 6:
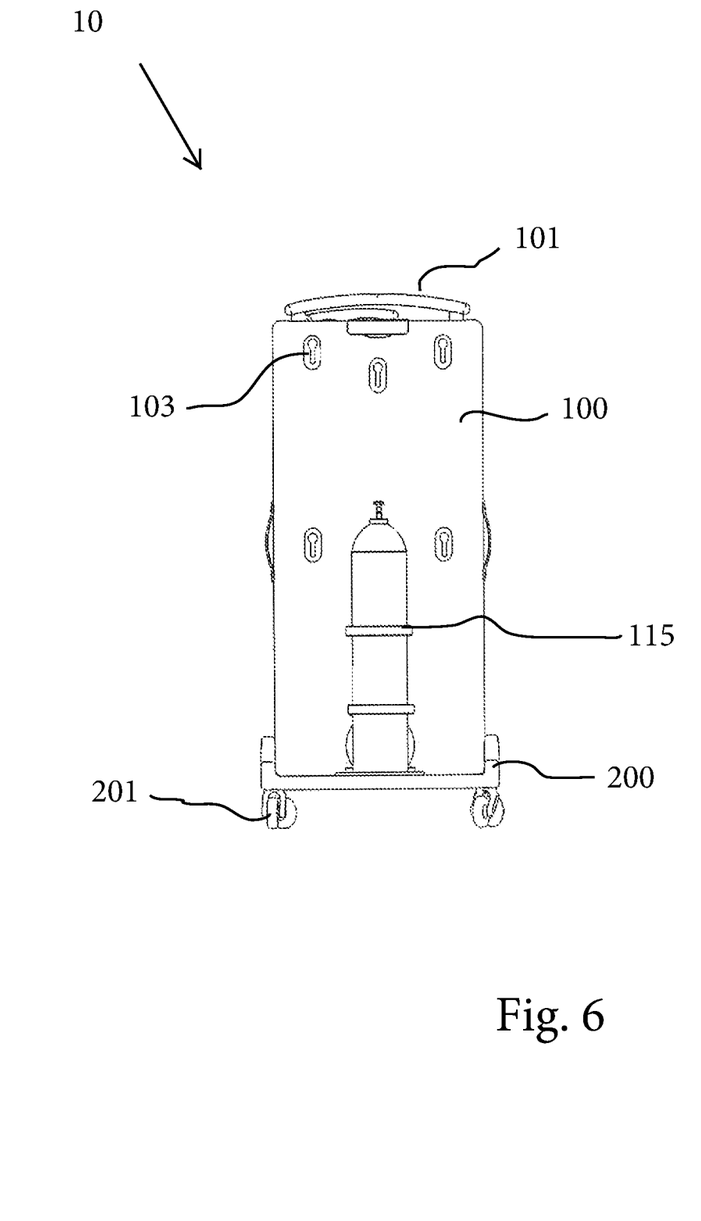
FIG. 6 shows a front side view of the cart with oxygen tank attachment, according to the present invention.
Figure 7:
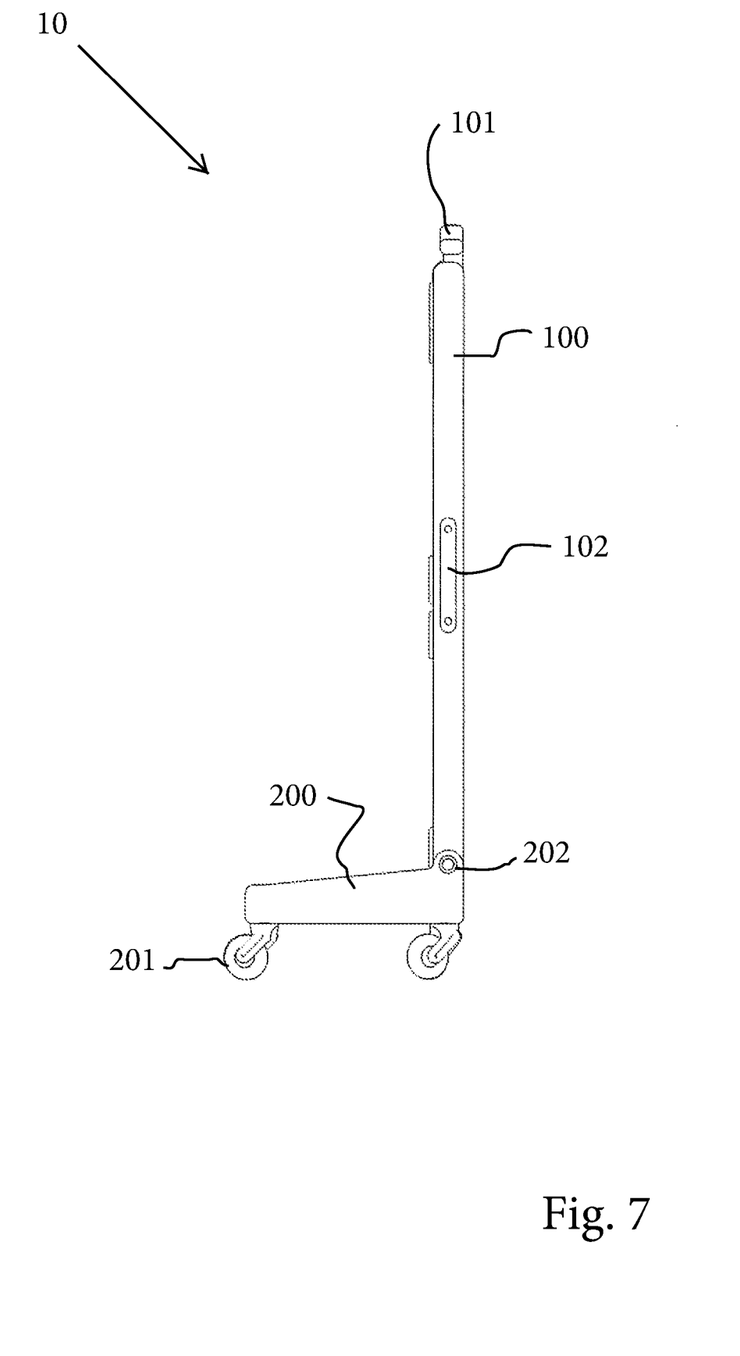
FIG. 7 shows a side view of the cart, according to the present invention.

The center portion 100 includes a plurality of apertures 103. The apertures 103 preferably of a keyhole shaped and dispersed throughout the height and a width of the center portion 100 to allow for the securing of various attachments 110, 111, 112, 113, 114, 115 to the center portion 100. The keyhole shape of the apertures 103 generally have a wide portion tapering to a narrow portion, wherein the attachments 110-115 include tabs sized for receipt within the large portion of the keyhole shape 103 and slide into the narrow portion for locking and securing the attachments 10-15 to the device 10. These attachments include, but are not limited to, a small basket 110, a large basket 111, an IV retainer 112, a large mesh shopping bag 113, a small mesh shopping bag 114, and oxygen retainer rings 115. A flip-down oxygen ring 104 is located on the center portion 100 adjacent to the base portion 200 and allows for the securing of an oxygen tank (FIG. 6).

The base portion 200 may further include a raised and molded portion that is designed and sized to correspond to the size and shape of an oxygen canister, wherein the molded portion may replace the flip-down oxygen ring 104.

The center portion 100 is preferably constructed out of a durable material, such as polycarbonate, although other similar materials may be used. The device 10 can be configured for multiple uses through the use of various attachments 110-115.

The center portion 100 may include a hinged and drop-down panel opposite the apertures 103 on a backside of the center portion 100, wherein the panel reveals a storage compartment within a cavity of the center portion 100. Preferably, this storage compartment is designed and sized to store a lid member that is sized and shaped for receipt on an upper portion of the basket 110. This lid member may include an aperture sized for the placement of a beverage.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

I claim:

1. A multiple use assistive cart to aid in a users mobility, the cart designed for movement along a surface, the cart comprising:
    a center portion, the center portion extending a height opposite the surface and having:
        a handle, the handle located on a top side of the center portion opposite the surface, the handle extendable and including a braking lever; and
        a plurality of apertures, the apertures sized for the receipt and engagement of a plurality of attachments;
    a base portion, the base portion hingedly received on the center portion opposite the handle, the base portion and center portion movable to a folded position and an extended position, the base portion having a plurality of wheels, the plurality of wheels movable in multiple directions and affixed to the base portion opposite the center portion when in the extended position.

2. A multiple use assistive cart as in claim 1, wherein the apertures of the center portion are located along a side of the center portion and key-hole shaped and sized to a corresponding tab on the plurality of attachments.

3. A multiple use assistive cart as in claim 2, wherein the plurality of attachments are selected from a group of a small basket, a large basket, an IV retaining clip, a large mesh bag, a small mesh bag, and a retaining ring.

4. A multiple use assistive cart as in claim 1, wherein the wheels are caster style wheels and capable of 360 degrees of rotation.

5. A multiple use assistive cart as in claim 4, wherein the wheels are secured to the base portion through a resilient member, wherein the resilient member allows for a limited vertical direction of travel and provides for shock absorption during use.

6. A multiple use assistive cart as in claim 1, wherein the base portion includes raised portion resembling a ring, the raised portion extending a height opposite the surface the cart is placed upon.

7. A multiple use assistive cart as in claim 1, wherein a backside of the cart opposite the plurality of apertures includes a hinged access panel allowing for access to an interior cavity of the center portion for the storage of items, the items including a lid, the lid sized and shaped to correspond to the basket.

8. A multiple use assistive cart to aid in a users mobility, the cart designed for movement along a surface, the cart comprising:
    a center portion, the center portion extending a height opposite the surface and having:
        a handle, the handle located on a top side of the center portion opposite the surface, the handle extendable and including a braking lever; and
        a plurality of apertures, the apertures located on a side of the center portion, the apertures key-hole shaped and sized for the receipt and engagement of a plurality of attachments;
    a base portion, the base portion hingedly received on the center portion opposite the handle, the base portion and center portion movable to a folded position and an extended position, the base portion having a plurality of wheels, the plurality of wheels movable in multiple directions and affixed to the base portion opposite the center portion when in the extended position.

9. A multiple use assistive cart as in claim 8, wherein the plurality of attachments are selected from a group of a small basket, a large basket, an IV retaining clip, a large mesh bag, a small mesh bag, and a retaining ring.

10. A multiple use assistive cart as in claim 8, wherein the wheels are caster style wheels and capable of 360 degrees of rotation.

11. A multiple use assistive cart as in claim 10, wherein the wheels are secured to the base portion through a resilient member, wherein the resilient member allows for a limited vertical direction of travel and provides for shock absorption during use.

12. A multiple use assistive cart as in claim 8, wherein the base portion includes raised portion resembling a ring, the raised portion extending a height opposite the surface the cart is placed upon.

13. A multiple use assistive cart as in claim 8, wherein a backside of the cart opposite the plurality of apertures includes a hinged access panel allowing for access to an interior cavity of the center portion for the storage of items, the items including a lid, the lid sized and shaped to correspond to the basket.

* * * * *